US00PP24653P3

(12) United States Plant Patent
Coiner

(10) Patent No.: US PP24,653 P3
(45) Date of Patent: Jul. 22, 2014

(54) HYBRID TEA ROSE PLANT NAMED 'PARTY HARDY'

(50) Latin Name: *Rosa hybrida*
Varietal Denomination: Party Hardy

(76) Inventor: James W. Coiner, Covina, CA (US)

( * ) Notice: Subject to any disclaimer, the term of this patent is extended or adjusted under 35 U.S.C. 154(b) by 85 days.

(21) Appl. No.: 13/573,338

(22) Filed: Sep. 11, 2012

(65) Prior Publication Data

US 2014/0075611 P1 Mar. 13, 2014

(51) Int. Cl.
*A01H 5/00* (2006.01)

(52) U.S. Cl.
USPC ..... Plt./132

(58) Field of Classification Search
USPC ..... Plt./132
See application file for complete search history.

*Primary Examiner* — Annette Para
(74) *Attorney, Agent, or Firm* — Christie, Parker & Hale, LLP

(57) ABSTRACT

A new variety of Hybrid Tea rose suitable for garden decoration, having flowers of red and white coloration.

1 Drawing Sheet

Classification: The present invention relates to a new *Rosa hybrida* plant.

Variety denomination: The new plant has the varietal denomination 'PARTY HARDY'.

BACKGROUND OF THE INVENTION

This invention relates to a new and distinct variety of Hybrid Tea Rose. It has as its seed parent the variety known as unknown seedling and as its pollen parent the variety known as unknown seedling.

SUMMARY OF THE INVENTION

Among the features which distinguish the new variety from other presently available and commercial rose cultivars known to the inventor are the following combination of characteristics: The plant has a compact upright growing plant growth habit and is suitable for outdoor garden decoration.

Asexual reproduction of the new variety by budding as performed in Kern County shows that the foregoing and other distinguishing characteristics come true to form and are established and transmitted through succeeding asexual propagations. 'Party Hardy' may be asexually propagated by cuttings, budding and grafting. The budding and grafting successfully occurred on the plant/rootstock *Rosa hybrida* cv. 'Dr. Huey' (unpatented).

COMPARISON WITH THE CLOSEST COMMERCIALLY AVAILABLE CULTIVAR

The new variety may be distinguished from its closest commercially available cultivar, 'Perfume Tiger', by the following combination of characteristics: 'Party Hardy' has a lighter shade of pink, with slightly orange stripeds compared to 'Perfume Tiger', with much darker foilage.

BRIEF DESCRIPTION OF ILLUSTRATION

The accompanying photograph (FIG. 1) illustrates the new variety and shows the flowering thereof from bud to full bloom depicted in color as nearly correct as it is possible to make in a color illustration of the character. Throughout this specification, color references and/or values are based upon The Colour Chart of The Royal Horticultural Society (1966) except where common terms of color definition are employed.

DESCRIPTION OF THE NEW VARIETY

The following description is of 2 year-old rose plants of the new variety grown outdoors in Wasco, Calif. in the month of September. Phenotypic expression may vary with environmental, cultural and climatic conditions, as well as differences in conditions of light and soil.

FLOWER

The new variety sometimes usually bears its flowers singly. Flowers borne in regular clusters on strong, short to medium stems (about 1 inch to 1.5 inch). Outdoors, the plant blooms abundantly and nearly continuously during the growing season. The flowers have a slight tea fragrance.

BUD

The peduncle is about 2 inches in length, of average caliper (about ⅙ inch in diameter), and usually stiff. It is usually smooth, with very few stipitate glands, and very few hairs and prickles. Peduncle color is near between 143c and 143d.

Before the calyx breaks, the bud is about ¾ inch to about 1 inch in diameter at the widest point, about 2 inches to about 2½ inches in length, with a conspicuous neck. The surface of the bud bears few foliaceous appendages, usually with slender bristle-like foliaceous parts extending beyond the tip of the bud about ¼ inch or more of its length. Bud color is near between 72b and 72c sometimes lightly suffused.

The sepals are about ¾ inch to about 1 inch in length and about ¼ inch in width at the widest point. The outer surface color of the sepal is near between 143a and 143b sometimes often lightly suffused. The inner surface color of the sepal is near between 143c and 143d and covered edged with fine wooly tomentum; sepal margins are lined with some stipitate glands and hairs.

The receptacle of the flower is of very short to medium length (about ⅛ inch to about ¼ inch) and very thin to average to heavy in caliper (about ⅛ inch to about ¼ inch in diameter). The receptacle is globular in form. Its surface is very smooth, with somewhat thin walls. The receptacle color is near between 142a and 143b.

As the petals open (after the calyx breaks), the bud is about 2½ inches to about 3 inches in diameter at the widest point, about 2¾ inches to about 3 inches in length, and somewhat urn-shaped in form. The color of the under and upper surfaces of the newly opened petals is near between 72c with stripes close too 155a and 72d with stripes close to 155a. The color of the upper surfaces of the newly opened petals is near between 72a and 72b.

BLOOM

When fully open, the bloom ranges from about 3½ inches to about 4 inches in diameter. Petalage is double with about 28 to 32 petals and no petaloids. When partially open, the bloom form is somewhat globular, and the petals are somewhat spiraled with petal edges moderately rolled outward. When fully open, the bloom form is somewhat cupped to globular, and the petals tightly cupped to undulated with petal edges somewhat rolled outward

PETALS

The substance of the petals is somewhat crisp and of moderately thin to medium, with upper surfaces somewhat satiny to velvety and under surfaces somewhat satiny to velvety. The petals are about ¾ inch to about 1 inch in length and about 1 inch to about 1¼ inches in width at the widest point. Petal margins are somewhat dentate.

The outer petals are somewhat round to oval

The inner petals are somewhat round to oval.

Petaloids are absent.

NEWLY OPENED FLOWER

The under and upper surface color of the outer petals is near between 58b and 58c with stripes near 3c. The upper surface color of the outer petals is near between 58b and 58c. At the point where the petal attaches, there is a small zone of near between 3c and 3d.

The under and upper surface color of the intermediate petals is near between 58b and 58c, with stripes near 3c. The upper surface color of the intermediate petals is near between 58b and 58c, with stripes near 3c.

The under and upper surface color of the inner petals is near between 58b and 58c, with stripes near 3c. The upper surface color of the inner petals is near between 58b and 58c, with stripes near 3c.

The under and upper surface color of the petaloids are similar in coloration to the upper and under surfaces of the intermediate and inner petals.

The general tonality of the newly opened flower is near between 58b and 58c, with stripes near 3c.

THREE-DAY OLD FLOWER

The under and upper surface color of the outer petals is near between 58b and 58c, with stripes near 3c. At the point where the petal attaches, there is a small zone near 3d.

The general tonality of the three-day-old flower is near between 58b and 58c, with a stripe near 3c.

In September in Wasco, Calif., blooms on the bush growing outdoors generally last about four to five days. Cut roses from plants grown outdoors and kept at normal indoor living temperatures generally last about four to five days.

MALE REPRODUCTIVE ORGANS

Stamens are average in number (average about 110) and are arranged regularly about the pistils. A few are mixed with petaloids or tucked in the calyx. The filaments are of somewhat short to medium length (about 1/32 inch to about 1/16 inch) most with anthers. Filaments are near between 7c and 7d in color. The anthers are somewhat small to medium for the class and all open approximately at the same time. Anther color is near between 7a and 7b when immature and near between 7c and 7d at maturity. There is no pollen.

FEMALE REPRODUCTIVE ORGANS

Pistils vary in number (average about 140). The styles are somewhat uneven, short in length (about 1/32 inch to about 1/16 inch), thin in caliper, and very loosely bunched. Stigma color is near between 6b and 6c. Style color is near between 6c and 6d. Ovaries are enclosed in the calyx although few may protrude from calyx.

Hips have not been observed on this variety when grown in Wasco, Calif.

FOLIAGE

The compound leaves are usually comprised of five to seven leaflets and are borne abundantly in normal quantities. The five-leaflet leaves are about 1¾ inch to about 2 inches in length and about ¾ inch to about 1 inch in width at the widest point, somewhat heavy in texture, and very glossy in finish. Their margins are somewhat serrate and irregular The upper and under surface color of the mature leaf is near between 141a and 141b. The under surface color of the mature leaf is near between 139b and 139c. The upper and under surface color of the young leaf is near between 141c and 141d. The under surface color of the young leaf is near between 139c and 139d.

The rachis is somewhat light in caliper and smooth. The upper side is deeply to moderately shallowly grooved with few hairs and stipitate glands and prickles on the edges of the grooves. The under side of the rachis is very smooth with few hairs and stipitate glands and very small prickles. The rachis color is near 147c.

The petiole is somewhat light in caliper and somewhat smooth. The upper side is shallowly grooved with few hairs and stipitate glands and prickles on the edges of the grooves. The under side of the rachis is somewhat smooth with few hairs and stipitate glands and moderately small prickles. The petiole is about ⅛ inch to about ¼ inch in length and about 1/16 inch in diameter at the widest point. The petiole color is near between 137b and 137c.

The plant displays an above average degree of resistance to powdery mildew and rust as compared to other commercial varieties grown under comparable conditions in Wasco, Calif. The plant's winter hardiness and drought/heat tolerance are yet to be determined.

GROWTH

The plant has a compact upright medium growth habit (about 3.5 ft. to about 4 ft. in height and about 2.5 ft. to about 3 ft. spread at the widest point), with full branching. It displays vigorous growth and the canes are of light to medium caliper for the class.

The color of the major stems is near between 141b and 141c. They do not bear prickles.

The color of the branches is near between 140a and 140b. There are no coarse hairs.

The color of the new shoots is near between 53b and 53c suffused with 141c and 141d. They bear no prickles

I claim:

1. A new and distinct Hybrid Tea rose plant of the variety substantially as described and illustrated herein.

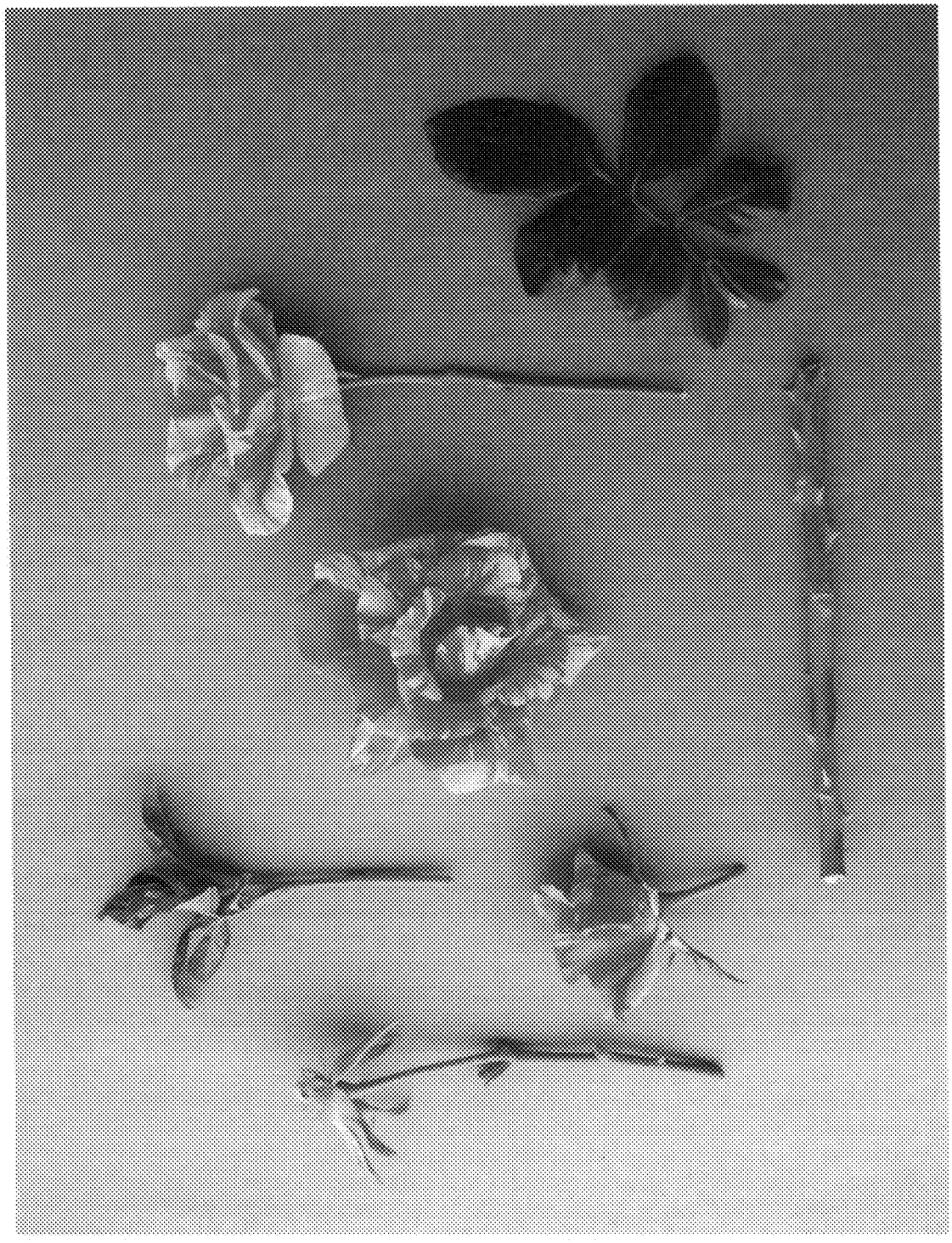

* * * * *